(12) United States Patent
Negus et al.

(10) Patent No.: US 6,902,562 B1
(45) Date of Patent: Jun. 7, 2005

(54) PERCUTANEOUS MYOCARDIAL REVASCULARIZATION MARKING AND THERAPEUTIC OR DIAGNOSTIC AGENT DELIVERY SYSTEM

(75) Inventors: Charles Christopher Negus, Taunton, MA (US); Stephen J. Linhares, Taunton, MA (US); Robert I. Rudko, Holliston, MA (US); Eileen A. Woodruff, Whitinsville, MA (US); Robert R. Andrews, Norfolk, MA (US)

(73) Assignee: PLC Medical Systems, Inc., Franklin, MA (US)

( * ) Notice: Subject to any disclaimer, the term of this patent is extended or adjusted under 35 U.S.C. 154(b) by 0 days.

(21) Appl. No.: 09/493,423

(22) Filed: Jan. 29, 2000

Related U.S. Application Data

(63) Continuation-in-part of application No. 08/731,862, filed on Oct. 21, 1996, now Pat. No. 6,030,377.

(51) Int. Cl.$^7$ ............................................. A61B 18/18
(52) U.S. Cl. ............................... 606/7; 606/10; 606/14; 606/15; 607/88; 607/89
(58) Field of Search ..................... 606/7, 10, 13–16, 606/41, 45, 49; 607/88, 89, 92; 604/27, 48, 604/93.1, 99.01, 103; 128/898

(56) References Cited

U.S. PATENT DOCUMENTS

| | | | |
|---|---|---|---|
| 4,448,188 A | | 5/1984 | Loeb |
| 5,293,868 A | * | 3/1994 | Nardella ...................... 128/642 |
| 5,380,316 A | * | 1/1995 | Aita et al. ...................... 606/7 |
| 5,389,096 A | * | 2/1995 | Aita et al. ..................... 606/15 |
| 5,462,544 A | | 10/1995 | Saksena et al. |
| 5,464,404 A | | 11/1995 | Abela et al. |
| 5,586,982 A | * | 12/1996 | Abela .......................... 606/28 |
| 5,725,523 A | * | 3/1998 | Mueller ....................... 606/15 |
| 5,769,843 A | * | 6/1998 | Abela et al. .................. 606/10 |
| 5,840,059 A | * | 11/1998 | March et al. ................. 604/53 |
| 5,873,366 A | * | 2/1999 | Chime et al. ............... 128/898 |
| 5,891,133 A | * | 4/1999 | Murphy-Chutorian ......... 606/7 |
| 5,925,012 A | * | 7/1999 | Murphy-Chutorian et al. ........................... 604/30 |
| 5,957,916 A | * | 9/1999 | Jeevanandam et al. ....... 606/15 |
| 6,023,638 A | * | 2/2000 | Swanson ..................... 600/510 |
| 6,030,377 A | * | 2/2000 | Linhares et al. ............... 606/7 |
| 6,056,743 A | * | 5/2000 | Ellis et al. ................... 606/15 |

FOREIGN PATENT DOCUMENTS

WO    WO 99/49926    10/1999

* cited by examiner

Primary Examiner—A. Farah
(74) Attorney, Agent, or Firm—Iandiorio & Teska

(57) ABSTRACT

A system and method of marking percutaneous myocardial revascularization channels in a human heart and introducing into the channels a therapeutic or diagnostic agent by inserting a catheter system into the left ventricle of a heart, applying tissue ablative energy through the catheter to create a channel into the heart wall, introducing an imaging medium to the heart wall proximate the channel for marking the position of that channel for imaging, and introducing in or proximate the channel a therapeutic or diagnostic agent.

3 Claims, 12 Drawing Sheets

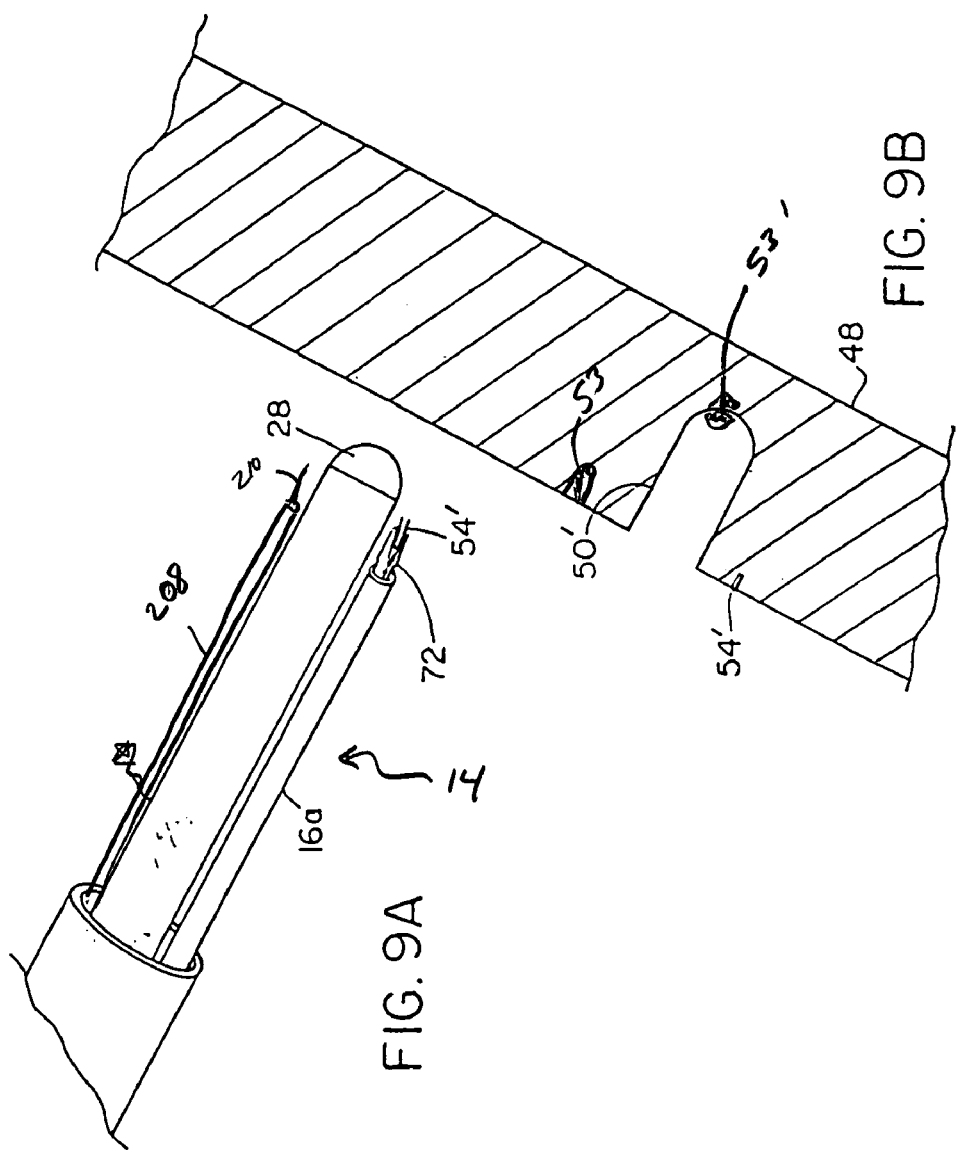

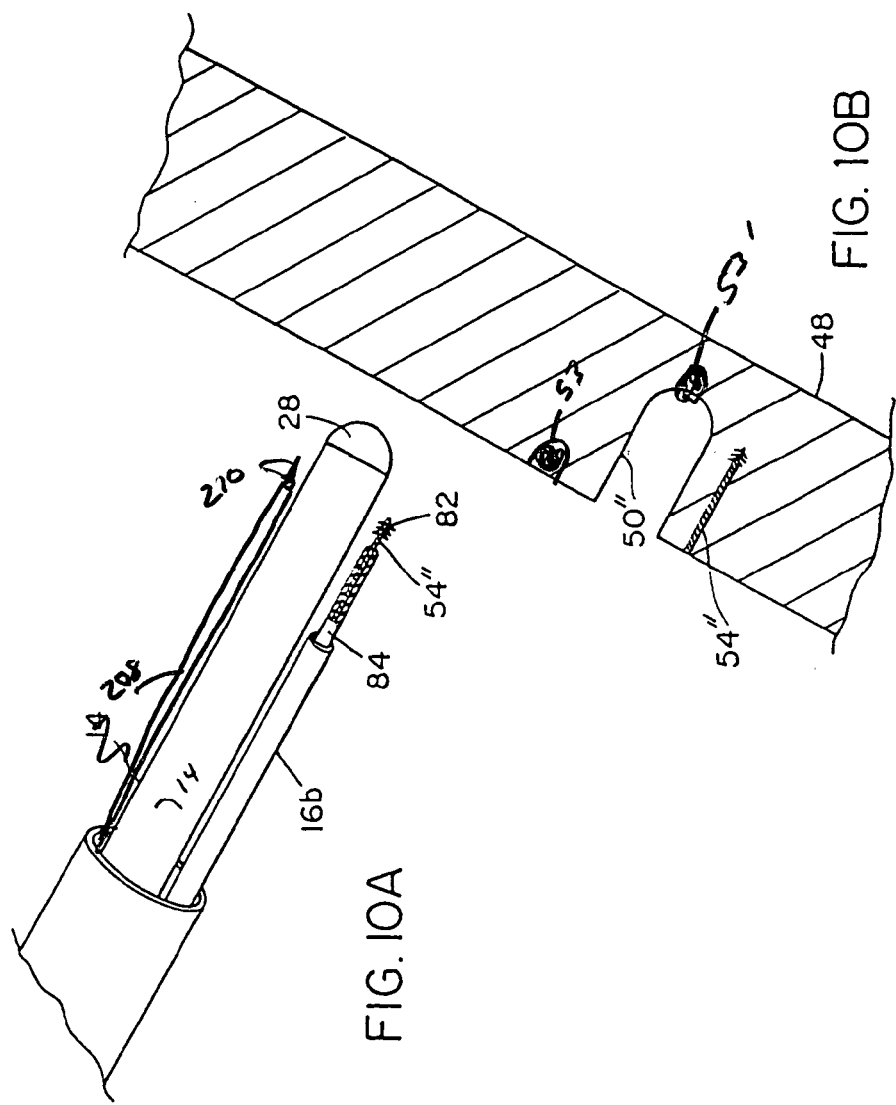

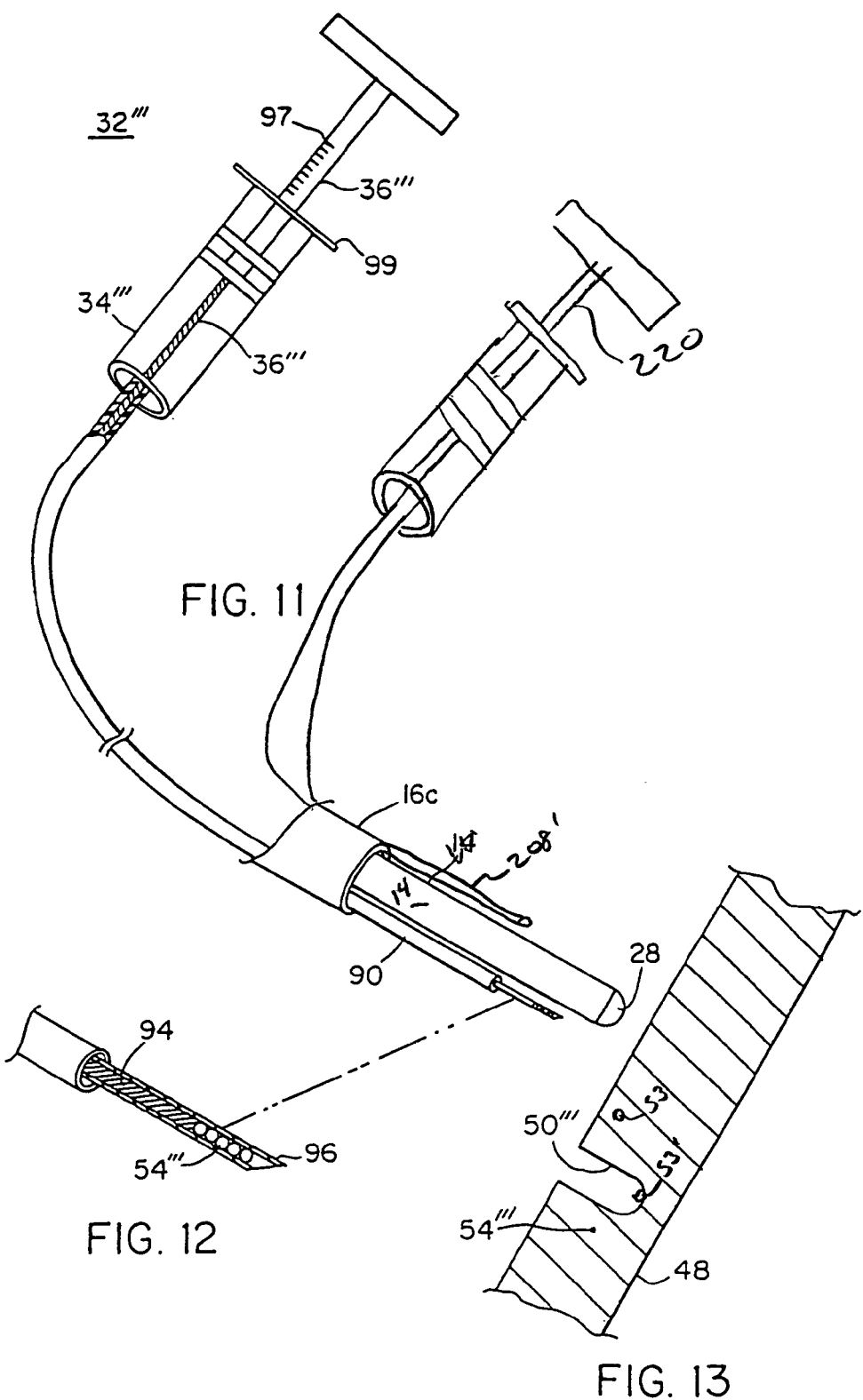

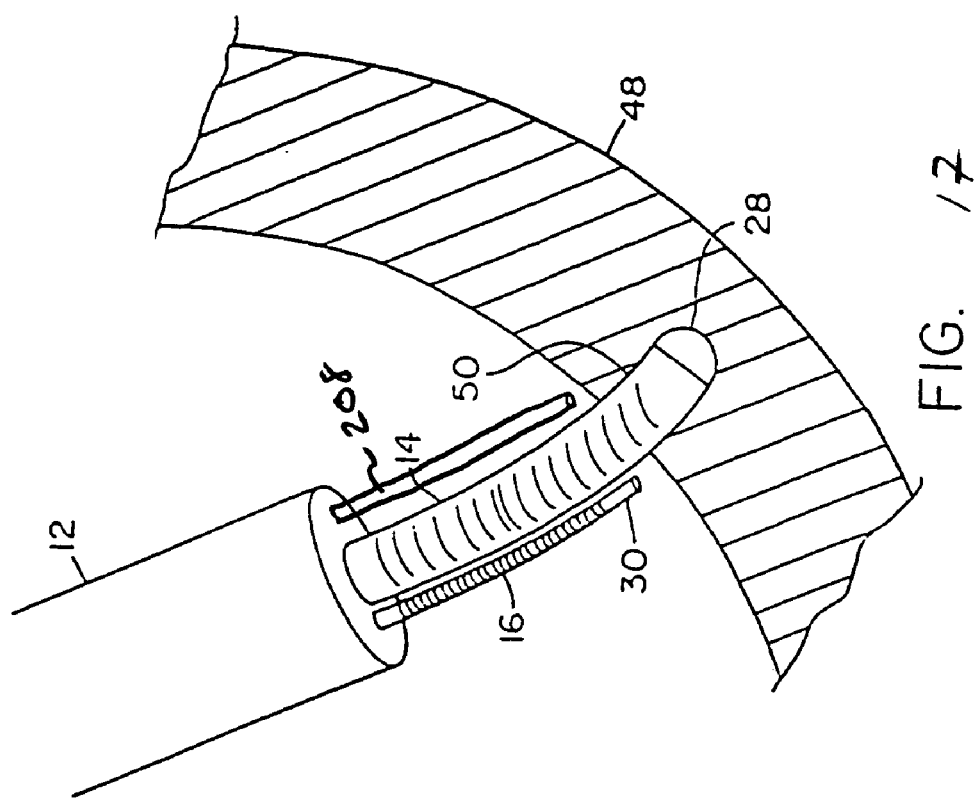

PERCUTANEOUS MYOCARDIAL REVASCULARIZATION MARKING AND THERAPEUTIC OR DIAGNOSTIC AGENT DELIVERY SYSTEM

RELATED APPLICATION

This application is a continuation-in-part application of U.S. Ser. No. 08/731,862 filed Oct. 21, 1996 now U.S. Pat. No. 6,030,377, entitled "Percutaneous Transmyocardial Revascularization Marking System", by Linhares et al.

FIELD OF THE INVENTION

This invention relates to a percutaneous channel marking and drug delivery system and method.

BACKGROUND OF THE INVENTION

Myocardial revascularization is presently accomplished using a laser to create channels in the wall of the left ventricle of the heart to perfuse the ischemic myocardium, thereby supplying blood and oxygen directly to the heart muscle, instead of installing one or more bypasses or using angioplasty to overcome blocked arteries and reinstate adequate blood flow. In the transmyocardial approach, a $CO_2$ laser is used to create channels from the outside of the heart wall to the inside. The channels heal rapidly on the outside, from digital pressure applied to the outside surfaces, leaving blind channels extending from the inside part way through the heart wall. During surgery, the surgeon can see each channel and carefully choose subsequent channel sites with correct spacing between them and avoid the danger of cutting a new channel too close to an existing one.

In the percutaneous approach, a Holmium or excimer laser supplies energy through a fiber optic element in a catheter to the inside of the left ventricle where channels are cut in the heart wall from the inside toward but hopefully never reaching the outside of the wall: unlike channels cut from the outside in using a $CO_2$ laser, channels cut from the inside through to the outside using Holmium or excimer lasers do not heal easily. Thus a channel cut through to the outer wall will cause a serious leak, pouring blood into the pericardium. This requires immediate emergency action, namely, open heart surgery to suture or apply a tamponade to the hole; otherwise the patient will die within a few minutes. Since, when working from the inside out using a catheter, a surgeon cannot see exactly where the fiber optic element is aimed nor can he tell where the previous channels have been cut, he constantly runs the risk of cutting a new channel next to, overlapping or even right on an existing channel, which can result in accidentally cutting right through the heart wall.

Moreover, although others have devised systems for delivering therapeutic or diagnostic agents into the channels, no device exists for simultaneously marking the channels and introducing into the channels a therapeutic or diagnostic agent. See U.S. Pat. Nos. 5,840,059; 5,925,012, and international application PCT/US99/07081 incorporated herein by this reference. Indeed, if the channels cannot be seen, it is difficult to introduce a therapeutic drug into the channels.

SUMMARY OF THE INVENTION

It is therefore an object of this invention to provide a percutaneous channel marking and drug delivery system and method.

It is a further object of this invention to provide such a percutaneous channel and drug delivery marking system which enables a surgeon to see the existing channels using standard imaging techniques.

It is a further object of this invention to provide such a percutaneous channel marking system which, when cutting channels from the inside out, avoids the possibility of cutting channels too close, overlapping, or right on an existing channel and avoids the possibility of cutting a channel too far and through the heart wall.

It is a further object of this invention to provide such a percutaneous channel marking system which enables channels to be cut from the inside out in an organized pattern with proper placement and spacing.

It is a further object of this invention to provide such a percutaneous channel marking system which creates a temporary or permanent record of the channel placement for future reference, therapy, autoptic analysis, and for the introduction of a therapeutic or diagnostic agent.

The invention results from the realization that a truly safe and effective system and method for marking percutaneous transmyocardial revascularization channels created in the heart wall can be achieved by placing an imaging medium proximate each channel to enable a surgeon to see existing channels using standard imaging techniques, and place the channels in an organized pattern with proper placement and spacing. This invention results from the further realization that now that the channels can be seen, it is easier to introduce a therapeutic or diagnostic agent into or proximate the channels.

This invention features a percutaneous myocardial revascularization marking and therapeutic or diagnostic agent delivery system. A treatment catheter having a proximal end is interconnected with a source of tissue ablative energy and has a distal end for applying that energy to the heart wall to create a channel therein. The system includes a channel marking and drug delivery catheter subsystem connected to an imaging medium source and a source of a therapeutic or diagnostic agent. The distal end of the catheter subsystem is disposed proximate the distal end of the treatment catheter for applying both an imaging medium and the therapeutic or diagnostic agent in or proximate the channel.

In one embodiment, the channel marking and drug delivery catheter subsystem includes two catheters: one marking catheter having a distal end proximate the treatment catheter for applying the imaging medium, and a therapeutic or diagnostic agent delivery catheter having a distal end proximate the treatment catheter for applying the therapeutic or diagnostic agent in or proximate the channel.

This invention also features a method of marking and delivery to a percutaneous myocardial revascularization channel a therapeutic or diagnostic agent, the method comprising inserting a catheter into a chamber of a heart of a patient; applying tissue ablative energy through said catheter to create a channel in the heart wall; introducing to the heart wall in or proximate the channel an imaging medium for marking the position of that channel for imaging; viewing said imaging medium via an external imaging device positioned outside of said patient; and introducing to the heart wall proximate the channel or in the channel a therapeutic or diagnostic agent.

BRIEF DESCRIPTION OF THE DRAWINGS

Other objects, features and advantages will occur to those skilled in the art from the following description of a preferred embodiment and the accompanying drawings, in which:

FIG. 9A is an enlarged three-dimensional schematic view of the tip of a marking catheter for introducing staple markers into the heart wall and of the drug delivery catheter;

FIG. 9B is a sectional view of a portion of the heart wall after a channel has been cut, a marker staple has been installed, and a drug delivered;

FIG. 10A is a view similar to FIG. 9A showing a marker catheter for inserting marker sutures into the heart wall and a drug delivery catheter;

FIG. 10B is a view similar to FIG. 9B showing a marker suture installed in the wall of the heart and a drug proximate the channel;

FIG. 11 is a view similar to FIGS. 9A and 10A showing a marker catheter for introducing radiopaque beads and drug delivery beads into a heart wall;

FIG. 12 is an enlarged detailed partially sectional view of the tip of the marker catheter of FIG. 11 showing the plunger and a bead about to be dispensed;

FIG. 13 is a view similar to FIGS. 9B and 10B showing a heart wall with the channel cut into it, a marker radiopaque bead and a drug delivery bead adjacent the channel;

FIG. 17 is a view showing the marking catheter and drug delivery catheter in place inside the heart.

DISCLOSURE OF THE PREFERRED EMBODIMENT

Figure 1:
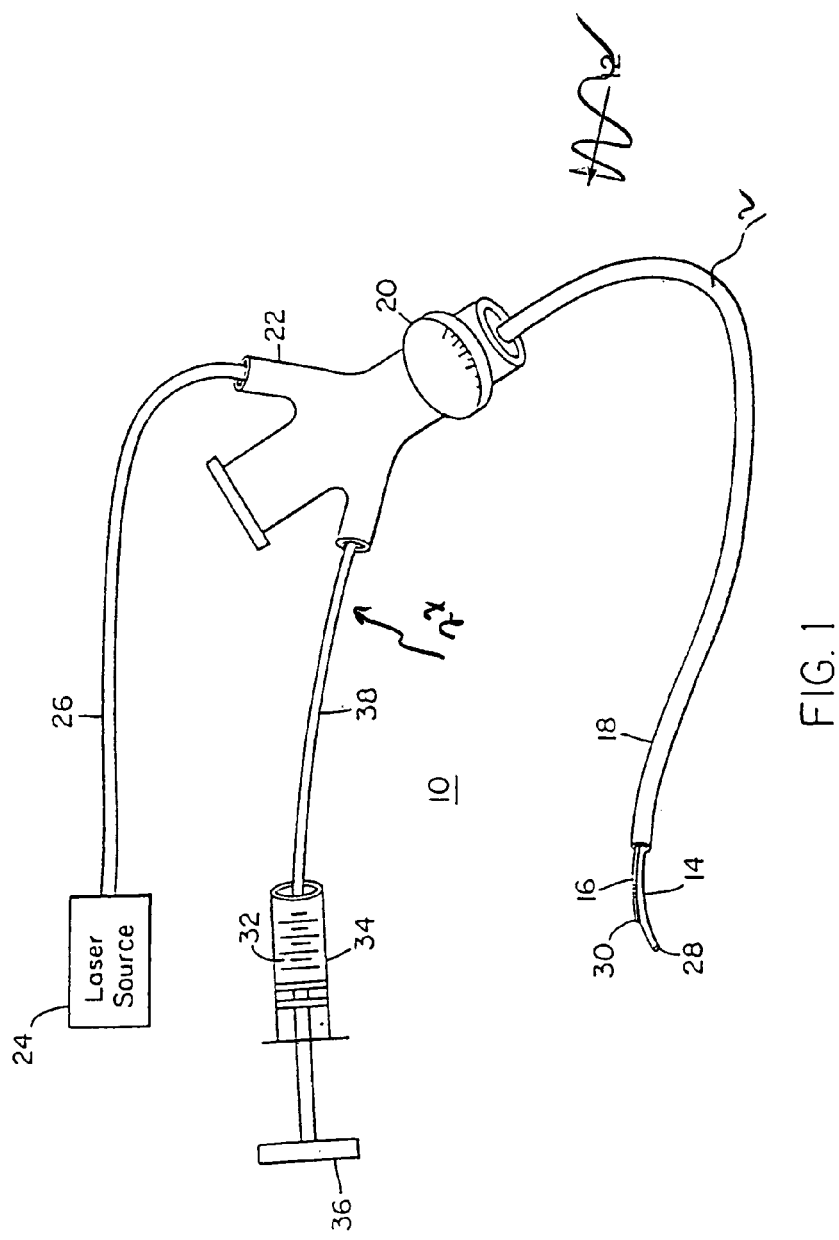
FIG. 1 is a schematic diagram of a percutaneous myocardial revascularization marking and drug delivery system according to this invention.

There is shown in FIG. 1 a percutaneous transmyocardial revascularization marking and therapeutic or diagnostic agent delivery system 10 according to this invention including treatment catheter 14 and channel marking and drug delivery catheter subsystem 27 inside lumen 12. The tip 18 of lumen 12 is aimed or manipulated by means of knob 20 in the manner of conventional catheter control. Knob 20 is mounted on control 22 which interconnects treatment catheter 14 to a source of tissue ablative energy. In this case, the source of tissue ablative energy is a laser 24 which provides the laser beam through laser catheter 26 which may, for example, be a fiber optic element. The laser beam is then delivered to treatment catheter 14 which may also be a fiber optic element with a lens 28 at its distal end.

Catheter 16 may include a needle or cannula at its distal end or tip 30 for dispensing a dye which is radiopaque, or X-ray opaque, so that it may be recognized through techniques of nuclear magnetic resonance, X-ray fluoroscopy or similar imaging techniques. The catheter also functions to dispense a therapeutic or diagnostic agent. The dye and the therapeutic or diagnostic agent may be simultaneously injected using syringe 32 that includes a body 34 and plunger 36. The dye and the therapeutic or diagnostic agent may be a liquid which is delivered through conduit 38 and control 22 to catheter 16.

Figure 2:
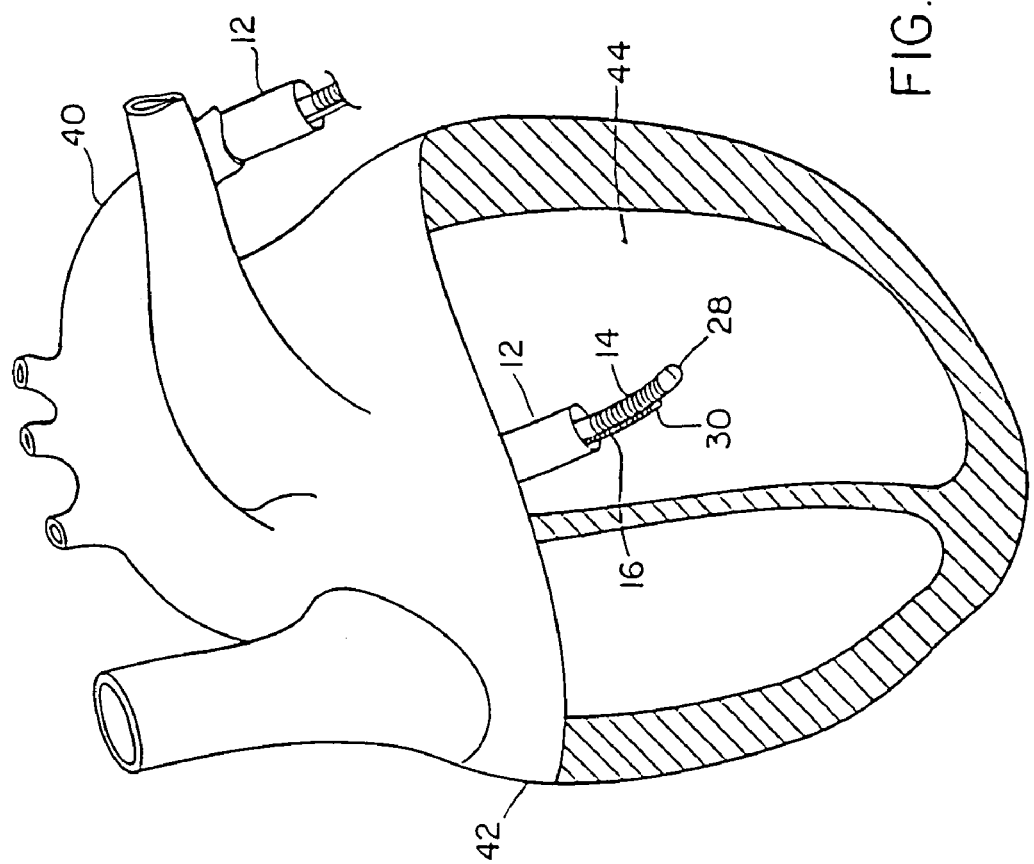
FIG. 2 is an enlarged schematic partially sectional view of a human heart with the system of FIG. 1 engaged with the left ventricle.
Figure 4:
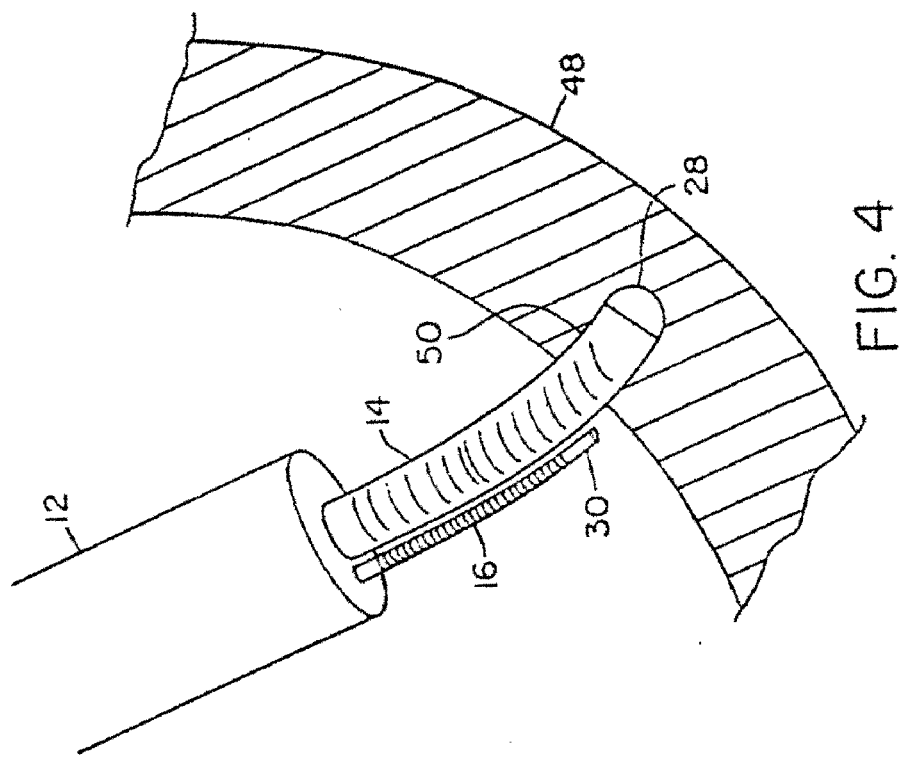
FIG. 4 is a view similar to FIG. 3 after the ablative energy has been applied and a channel has been cut into the heart wall.

Lumen 12 is threaded through the aorta 40, FIG. 2, of human heart 42 so that the lens 28 of treatment catheter 14 and the tip 30 of catheter 16 are inside left ventricle 44. By manipulating knob 20 on control 22, lens 28 of treatment catheter 14 is placed against the surface 46, FIG. 3, of heart wall 48 and laser 24 is energized. This provides ablative energy at heart wall 48 and creates a channel 50, FIG. 4, in heart wall 48.

Figure 5:
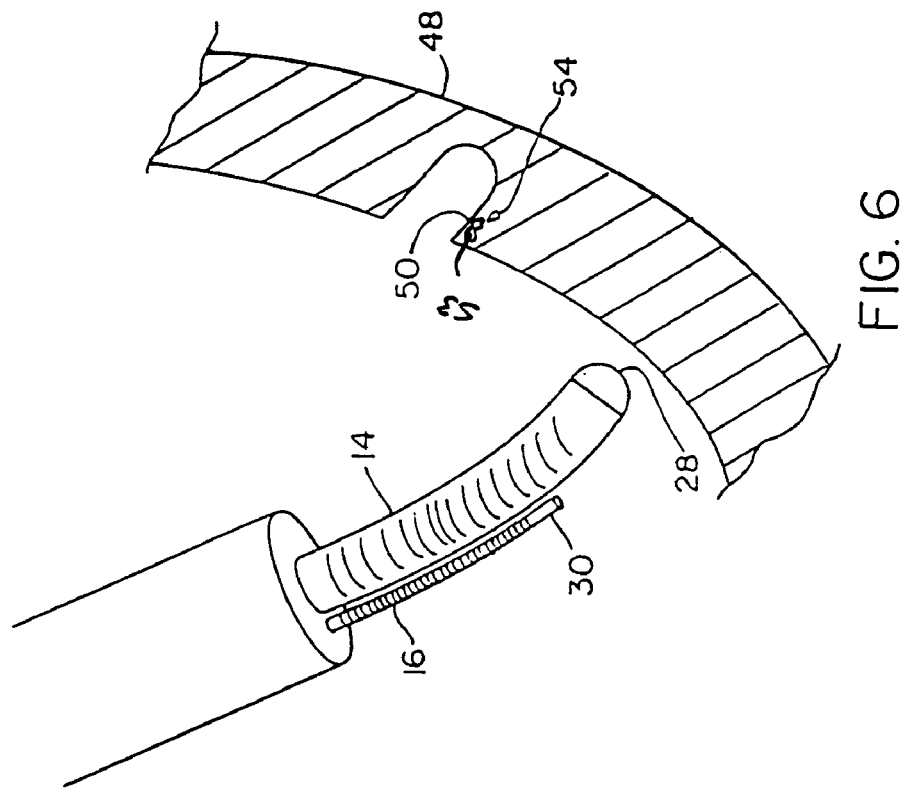
FIG. 5 is a view similar to FIG. 4 with the treatment catheter still in place and the combined marking and drug delivery catheter actuated to introduce a drop of dye and a therapeutic or diagnostic agent into the heart wall proximate the channel.

With the tip 28 of treatment catheter 14 still resident in channel 50, FIG. 5, a needle or cannula 52 is extended from tip 30 of catheter 16 to inject a drop of imaging dye 54 and a therapeutic or diagnostic agent 53 into heart wall 48 proximate channel 50. This is accomplished by actuating plunger or piston 36, FIG. 1 of syringe 32 so that a predetermined amount of fluid is forced out of cylinder or body 34 through conduit 38 through catheter 16 and out the end of needle 52, FIG. 5. Subsequently, lumen 12 is withdrawn from channel 50, FIG. 6 leaving channel 50 marked by marker 54 made up of the radiopaque dye, for example and leaving therapeutic or diagnostic agent 53. In one embodiment marker 54 and agent 53 are combined in syringe 32, FIG. 1.

Delivery of therapeutic angiogenic agents to the channel site can promote vascularization of the site. VEGF, vascular endothelial growth factor, is an angiogenic agent which has the capability (in certain forms) of binding to the endocardium. Examples of angiogenic growth factors are VEGF, acidic and basic fibroblast growth factors (aFGF, bVGF), nerve growth factor (NGF), and monocite chemoattractant protein-1 (MCP-1), Angiopoietin-1 (Ang-1), Angiopoietin-2 (Ang-2), Adnovirus vector expressing complementary DNA for VEGF (AdVEGF), VEGF 121, AdVEGF 121.10, AdFGF 4, VEGF-C, Plasmid phVEGF-165, Insulin growth factor I (IGF-I), Insulin growth factor II (IGF-II), VEGF 165, Acidic fibroblast growth factor (aFGF), and Basic fibroblast growth factor (FGF). The therapeutic and diagnostic agents disclosed in U.S. Pat. Nos. 5,840,059 and 5,925,012 and in PCT/US/07081 may also be used. Depositing the angiogenic agent in close proximity to channel 50, FIG. 6 increases the revascularization of ischemic myocardium.

The angiogenic agent may be in liquid form and injected alone or in combination with the radiopaque dye. Such an agent could also be in gel form to provide greater residence time in the heart and potentially greater therapeutic effect. The gel may be in the form of a polymeric based hydrogel, which is soluble in an aqueous environment. In such a form, the delivery pressure would be higher. The agent also could be in solid (bead or pellet form).

Dyes are temporary markers. For a more permanent mark a metal material may be used or a metal powder may be added to the dye. The radiopaque dye may be Renographin or an iodinated compound. Having noted the location of channel 50, FIG. 6 as indicated by marker 54, and having treated the channel with a therapeutic or diagnostic agent 53, the surgeon can now properly reposition the lens 28 at the tip of treatment catheter 14 at a new position on wall 48 spaced from channel 50 in preparation for the cutting of the next channel properly positioned and spaced with respect to channel 50 and all other channels previously cut and marked. After a number of such channels have been cut, marked, and treated, the section of the heart wall 48 will appear as in FIG. 7, with each channel 50, 50a, 50b, 50c, 50d and 50e marked by imaging medium 54, 54a, 54b, 54c, 54d and 54e and treated with therapeutic or diagnostic agent 53, 53a, 53b, 53c, 53d and 53e.

Figure 8:
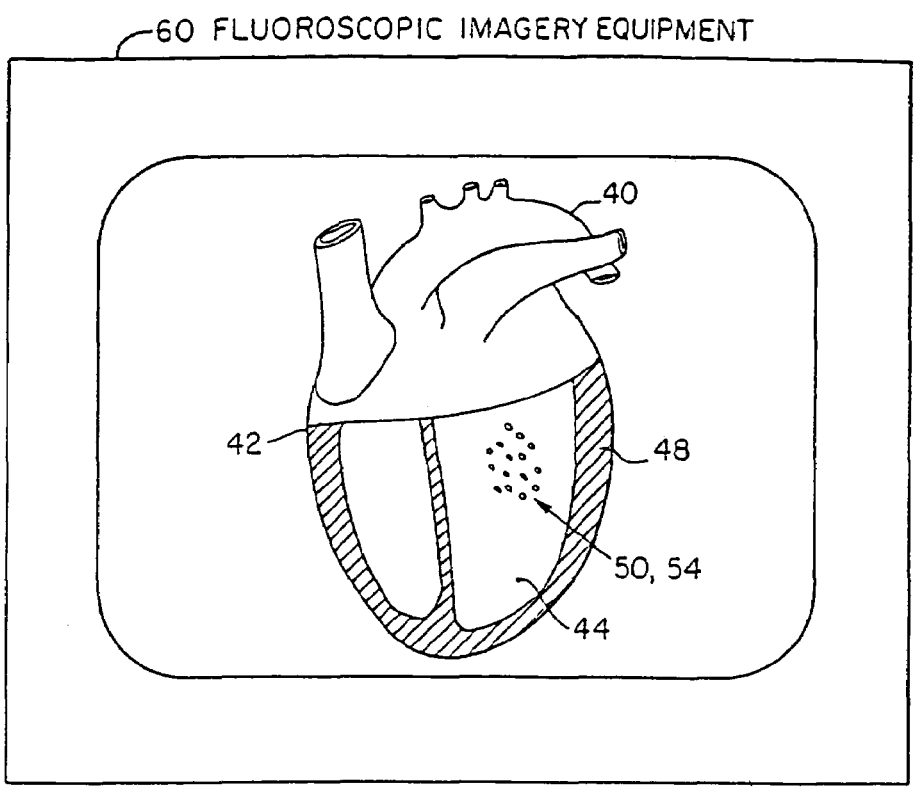
FIG. 8 illustrates a fluoroscopic image of a human heart displaying a number of markers indicating the position of channels in the heart wall.

The view seen by the surgeon on an electronic fluoroscope 60, FIG. 8, shows all of the imaging media 54 which mark the channels already cut into the heart wall and treated with the therapeutic or diagnostic agent. Utilizing this image, the surgeon can properly locate and space the next channel to be created with respect to all the previous marked channels.

Although thus far the imaging medium has been explained in terms of a fluoroscopic dye, this is not a necessary limitation of the invention. It may be a radiopaque dye or any suitable material which can be seen using standard imaging techniques. For example, a metal staple or permanent suture 54', FIG. 9A, may be manipulated by clamp 72 extending marking catheter 16a in a conventional way for insertion into the heart wall 48, FIG. 9B, proximate channel 50'.

In this embodiment, therapeutic or diagnostic agent delivery catheter 208 is separate from marker catheter 16b and includes needle 210. Needle 210 is used to deliver a suitable agent 53 proximate channel 50' or as shown at 53' in channel 50'.

In another configuration, a permanent suture 54", FIG. 10A, having barbs 82 at one end may be introduced via cannula 84 at the distal end of marker catheter 16b so that it becomes lodged in wall 48, FIG. 10B, next to channel 50" in heart wall 48. Sutures 54' or 54" may be made of any suitable material such as a radiopaque material, e.g., tantalum, platinum, gold, stainless steel. Drug delivery catheter 208 and needle 210 are again separate from marker catheter 16b and used to deliver therapeutic or diagnostic agent 53 proximate channel 50" or in channel 50" as shown at 53'—a process which is now much easier since channel 50" can be seen by virtue of marker 54".

In another alternative, cannula 90, FIG. 11, at the tip of catheter 16c is loaded with beads 54''', FIG. 12 which may be metal or fluorescing material or radiopaque material. A train of beads 54''' may be located in cannula 90 and as far back as desired in catheter 16c so that upon operation of plunger 36''' one or more beads 54''' will be dispensed by the piston 94 through the sharp end 96 of cannula 90 to be lodged in heart wall 48, FIG. 13. Gradations 97 in conjunction with the edge 99 of body 34''' allows dispensing of one or a selected number of beads 54'''. Similarly, agent delivery lumen 208' inside catheter 16c is loaded with beads of a therapeutic or diagnostic compound so that upon the operation of separate plunger 220 one or more beads of the agent will be lodged in the heart wall proximate channel 50''', as shown at 53 or in channel 50''', as shown at 53'. In this embodiment, lumen 208' is constructed the same as cannula 90 and includes a similar piston arrangement.

Figure 14A:
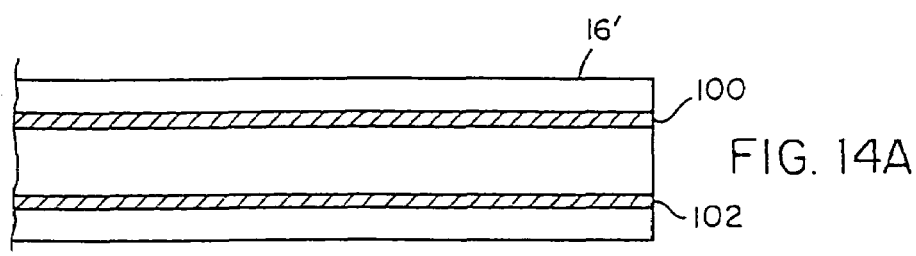
FIG. 14A is a side sectional view of a bipolar electrode tip for the treatment catheter.
Figure 14B:
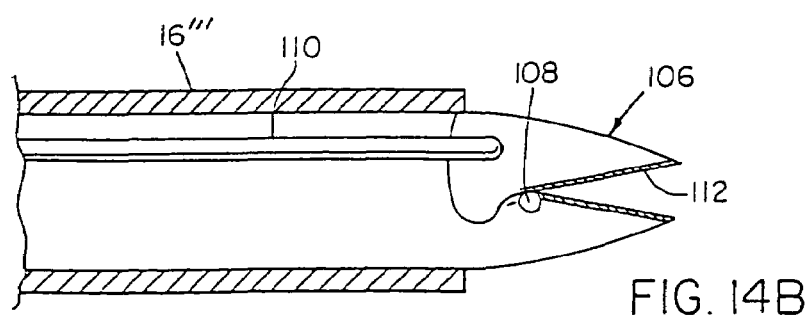
FIG. 14B is a view similar to FIG. 14A of the tip of the treatment catheter showing a scissor for ablating tissue.

Although thus far the invention has been disclosed in conjunction with an ablative device which uses laser energy conducted through a fiber optic element to produce the tissue ablation, this is not necessary. For example, as shown in FIG. 14A, the distal end of treatment catheter 16' may include a pair of conductors 100, 102 for providing an electric field across the tissue. In another construction, FIG. 14B, the distal end of treatment catheter 16'" may include scissors 106 pivoted at 108 with a control wire 110 attached to one of the jaws 112 and threaded back through catheter 16'" to the proximal end where it can be manipulated at control 22 to operate scissors 106.

Figure 3:
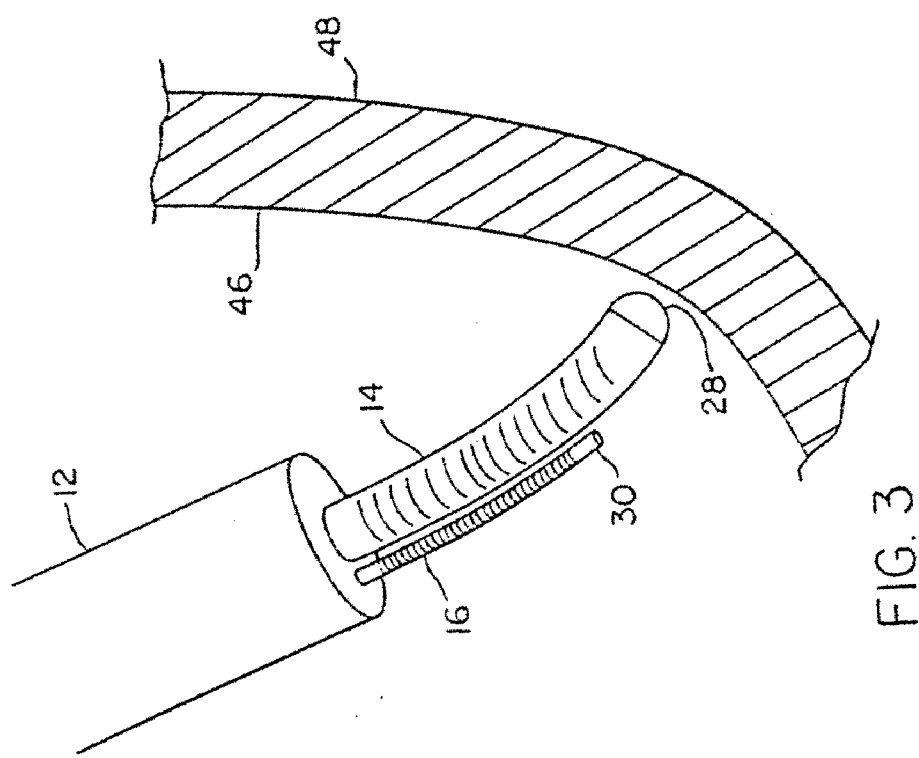
FIG. 3 is an enlarged detailed partially sectional view of a portion of the heart of FIG. 2 showing the treatment catheter in contact with the wall preparatory to application of the ablative energy.
Figure 6:
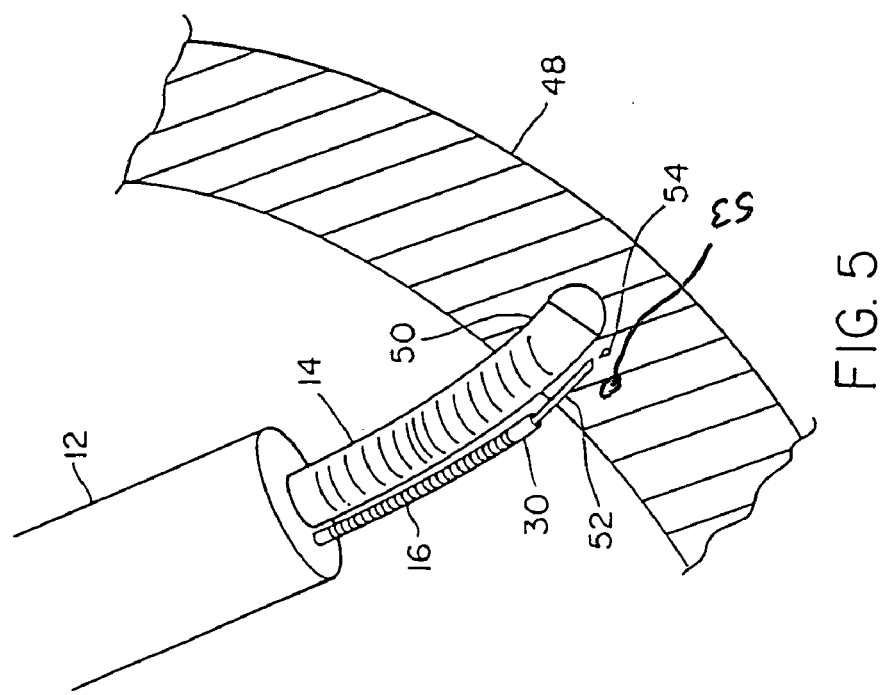
FIG. 6 is a view of the heart wall showing the channel after the catheter has been withdrawn and repositioned to make a subsequent channel.
Figure 7:
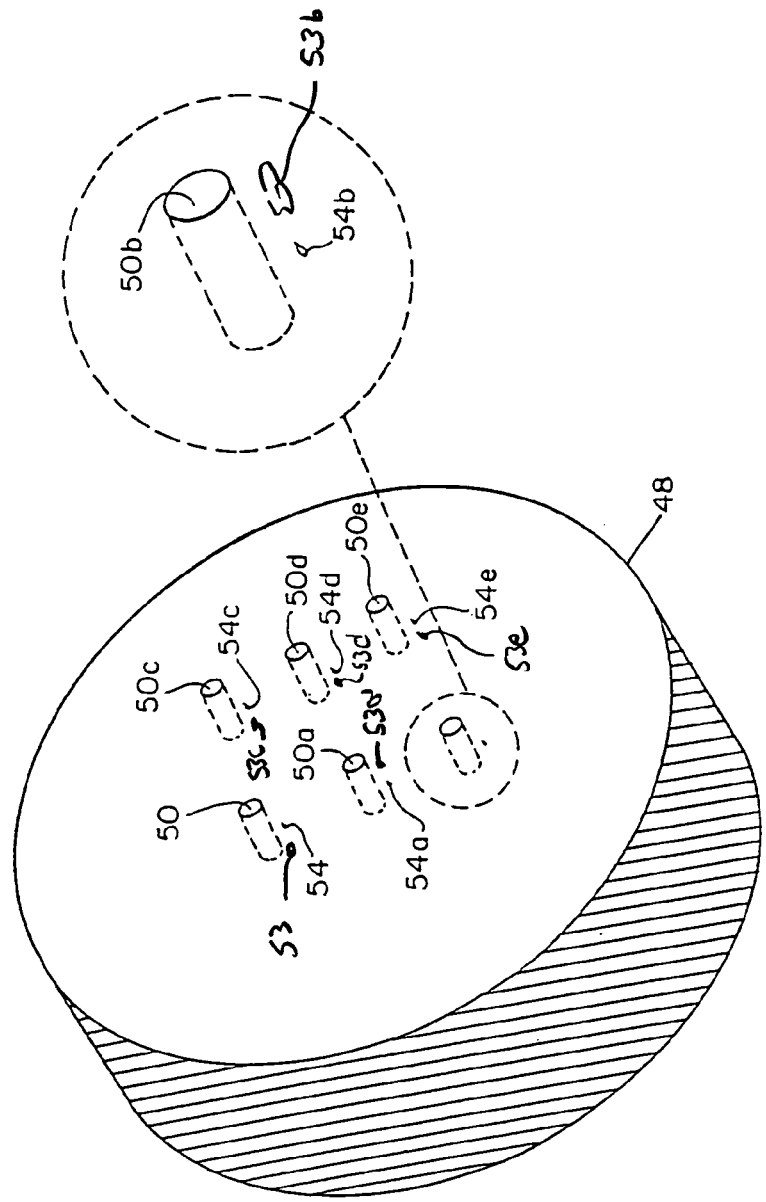
FIG. 7 is a diagrammatic three-dimensional view of a section of the heart wall showing a plurality of channels, adjacent markers, and adjacent therapeutic or diagnostic agents.
Figure 15:
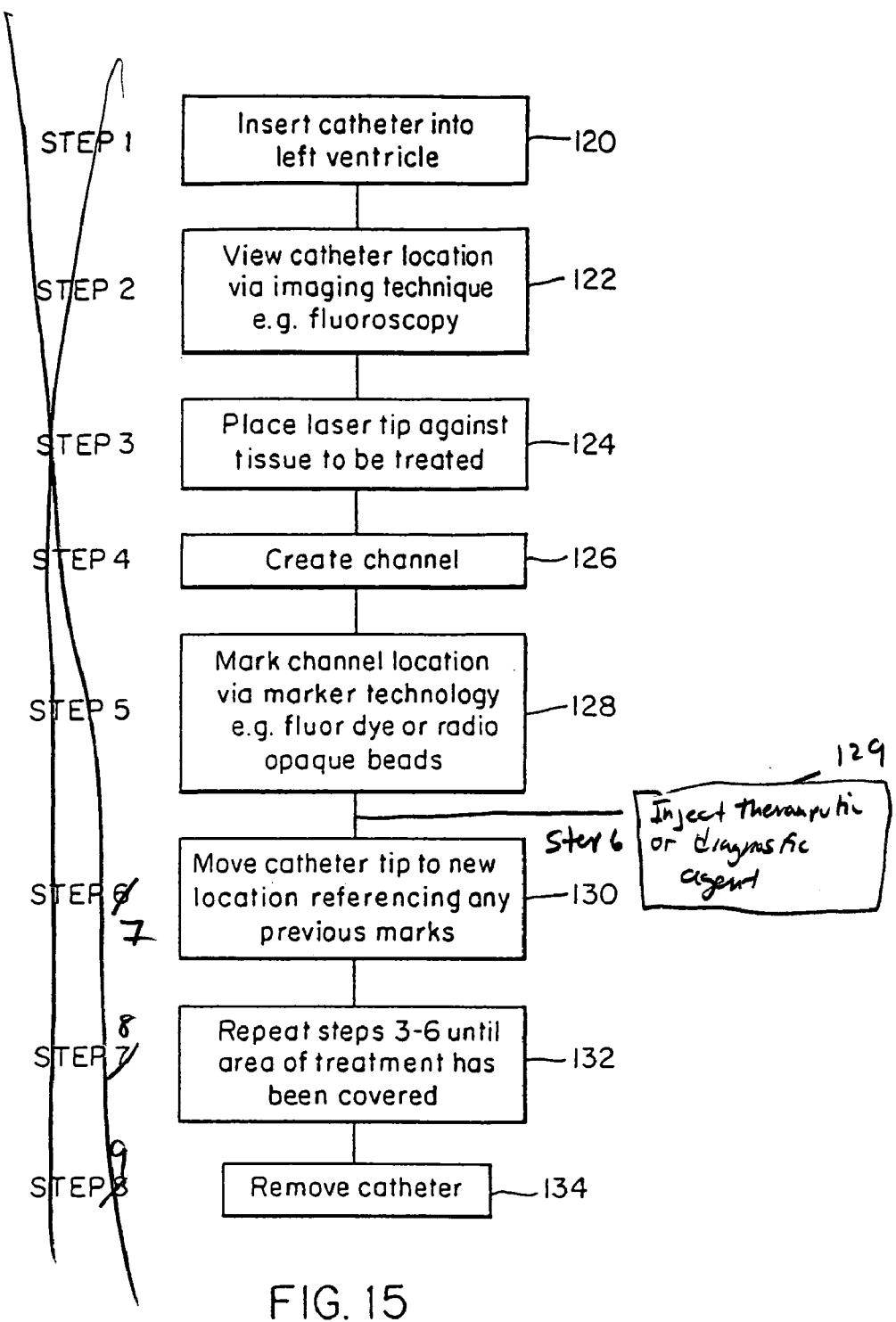
FIG. 15 depicts the steps and the method according to one embodiment of the method of this invention.

Channel marking and drug delivery is accomplished according to the method of this invention by inserting the catheter such as catheter system 12, FIG. 1 into the left ventricle of the heart, step 120 of FIG. 15, and then viewing the catheter location on a fluoroscope, for example, step 122, as shown in FIG. 8. The laser tip is then placed against the tissue to be treated, step 124, as shown in FIG. 3, and the ablative energy, for example from laser 24, FIG. 1, is provided to ablate the target tissue, step 126. The channel is then marked, step 128, and treated, step 129, sequentially or simultaneously as shown in FIG. 5, after which the catheter is removed, step 130, as shown in FIG. 6, leaving behind the newly created channel and its marker 54 and a therapeutic or diagnostic agent 53. These steps are done repeatedly, step 132, until the area of treatment has been covered with a predetermined pattern of properly located and spaced myocardial revascularization channels, after which the catheter is removed in step 134. The marker catheter may be made removable in order to replenish the supply of marking media such as beads, staples or dye without having to remove the treatment catheter. The drug delivery lumen may be constructed the same way.

Figure 16:
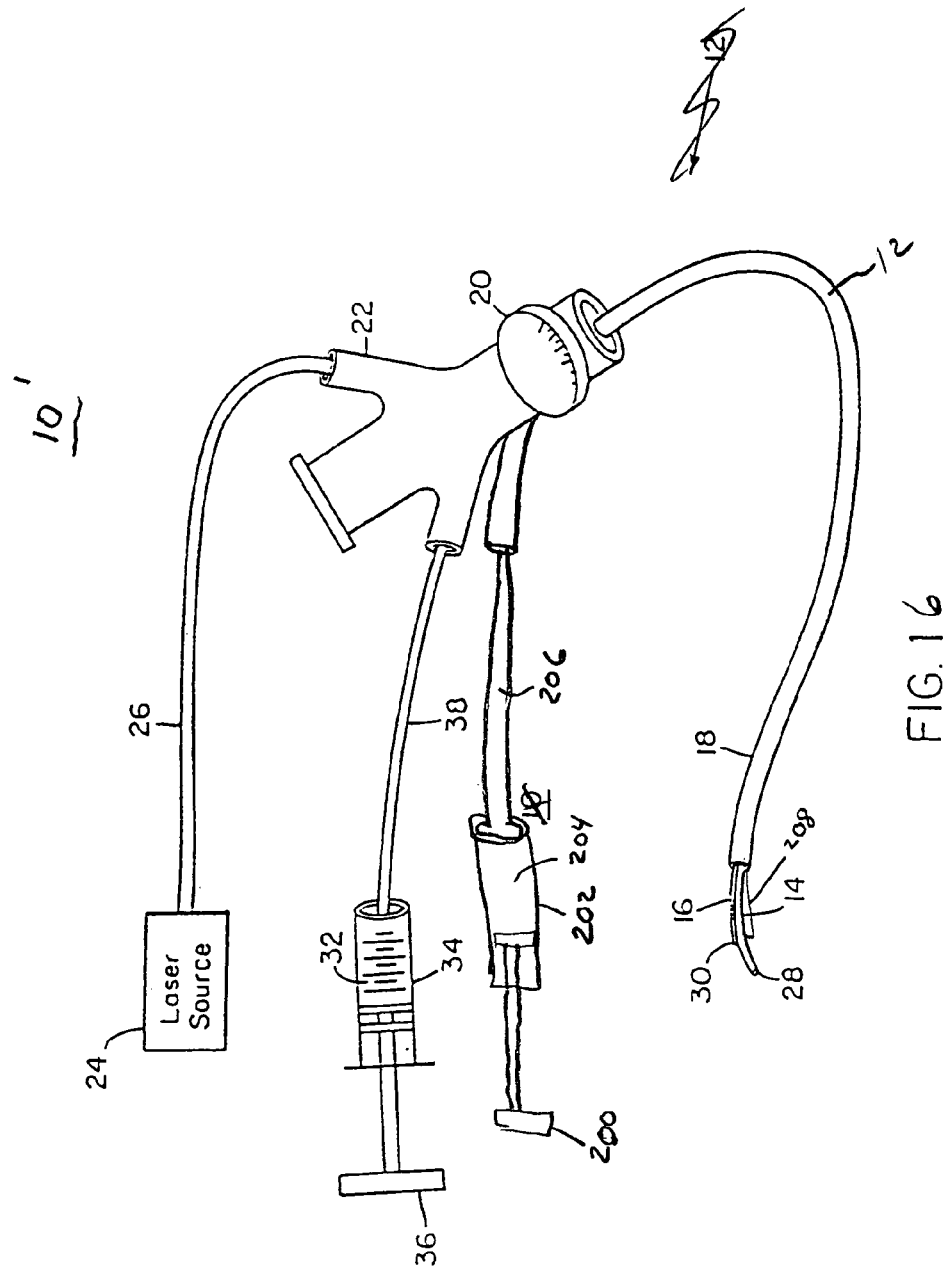
FIG. 16 is a schematic view of another embodiment of a channel marking and drug delivery system according to this invention.

As shown in FIG. 16, therapeutic or diagnostic agent catheter 208 extends inside lumen 12 next to treatment catheter 14 and marking catheter 16. Piston 200 of syringe 204 forces a predetermined amount of the drug in body 202 through catheter 208 in conduit 206 and out the end of a needle.

However, as delineated above, the marking substance and the therapeutic or diagnostic agent may be mixed in one syringe and in such an embodiment the marking and drug delivery functions are accomplished simultaneously.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A percutaneous myocardial revascularization marking and therapeutic or diagnostic agent catheter delivery system comprising:

a treatment catheter having a proximal end interconnected with a source of tissue ablative energy and a distal end for applying that energy to the heart wall to create a channel therein; and a channel marking and drug delivery catheter subsystem connected to an imaging medium source and a source of a therapeutic or diagnostic agent and having a distal end proximate the distal end of the treatment catheter for applying both an imaging medium and the therapeutic or diagnostic agent in or proximate the channel.

2. The system of claim 1 in which the channel marking and drug delivery catheter subsystem includes two catheters, one marking catheter having a distal end proximate the treatment catheter for applying the imaging medium, and a therapeutic or diagnostic agent delivery catheter having a distal end proximate the treatment catheter for applying the therapeutic or diagnostic agent in or proximate the channel.

3. A method of marking and delivery to a percutaneous myocardial revascularization channel a therapeutic or diagnostic agent, the method comprising:

inserting a catheter into a chamber of a heart of a patient;

applying tissue ablative energy through said catheter to create a channel in the heart wall;

introducing to the heart wall through said catheter in or proximate the channel an imaging medium for marking the position of that channel for imaging;

viewing said imaging medium via an external imaging device positioned outside of said patient; and introducing to the heart wall proximate the channel or in the channel a therapeutic or diagnostic agent.

* * * * *